United States Patent [19]

Bounias et al.

[11] Patent Number: 5,023,359
[45] Date of Patent: Jun. 11, 1991

[54] USE OF ORGANIC SALTS OF COPPER FOR THE TREATMENT OF HONEYBEE'S PARASITIC DISEASES

[75] Inventors: Michel Bounias, Cheval-Blanc; Jean F. Dufour, Versailles, both of France

[73] Assignee: Benechim, S.A., Lessines, Belgium

[21] Appl. No.: 538,030

[22] Filed: Jun. 13, 1990

[51] Int. Cl.$^5$ .................... A01K 47/00; A01N 59/20
[52] U.S. Cl. .................... 556/114; 556/113; 449/1; 43/124; 119/156; 514/6
[58] Field of Search .................... 556/110, 113, 114; 449/1; 43/124; 119/156, 160; 514/1, 6, 499

[56] References Cited
U.S. PATENT DOCUMENTS

| | | | |
|---|---|---|---|
| 3,846,460 | 11/1974 | Fite, Jr. | 556/114 |
| 4,603,214 | 7/1986 | Anderson et al. | 556/114 |
| 4,760,170 | 7/1988 | Gutierrez et al. | 556/114 X |
| 4,824,611 | 4/1989 | Cells | 556/114 X |

Primary Examiner—Arthur C. Prescott
Attorney, Agent, or Firm—Omri M. Behr

[57] ABSTRACT

Organic copper salts having the formula I

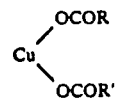

are used for the treatment of honeybees contaminated by various acarians and namely by the specific mite *Varroa jacobsoni*.

These salts are utilized either as such, or in the form of compositions containing them, optionally in admixture with diluents, nutritive ingredients and other active principles.

The compositions according to the invention are useful in the field of breeding and agriculture in restoring the sanitary condition in the hives.

8 Claims, 9 Drawing Sheets

USE OF ORGANIC SALTS OF COPPER FOR THE TREATMENT OF HONEYBEE'S PARASITIC DISEASES

SUMMARY OF THE INVENTION

This invention has as subject matter the use of at least, one organic copper salt having the formula I

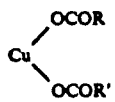

for the treatment of honeybees contaminated by various acarians and namely by the specific mite *Varroa jacobsoni*.

These salts are utilized either as such, or in the form of compositions containing them, optionally in admixture with diluents, nutritive ingredients and other active principles.

The compositions according to the invention are useful in the field of breeding and agriculture in restoring the sanitary condition in the hives.

PRIOR ART

The prior art is to the best of our knowledge illustrated by the following literature: Bounias M. and Popeskovic D. S., C. R. Soc. Biol., 180, (1980), 663-668.

PREFERRED EMBODIMENTS OF THE INVENTION

It is as subject matter of this invention the use of organic copper salts having the formula I

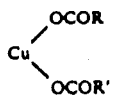

as well as compositions containing them, optionally in admixture with other active ingredients for treating the honeybees infested by various acarians and namely by a specific parasite, the mite *Varroa jacobsoni*.

During the last years, more and more significant deperishments have been stated in the population of the honeybees in numerous hives due to the fast extent of these parasites and namely *Varroa jacobsoni*. The treatment using the usual pesticides, more particularly the acaricides, apart from the fact that these pesticides cannot attack all the parasites, namely in the brood-comb show serious disadvantages. They are those bound to the possible contamination of the honey and wax by these compounds on one side, and those bound to the toxicity of these molecules for the honeybees the activity of which they decrease and even may cause the death.

Some pesticides moreover are not devoid of toxicity and cause a danger for the bee-keepers.

The role played by the metabolism of copper in the organism of the honeybee and the possibility to use it, to fight against *Varroa jacobsoni*, particularly by adding copper mineral salts such as copper sulphate in the nourishment or the feeding of honeybees, has been discussed in some scientific studies, especially in that of Bounias M. and Popeskovic D. S. in C. R. Soc. Biol 180 (1980) 663-668.

The use of such salts however affords only restricted possibilities for fighting this parasite, due to the fact that their structures are not well suited for the trans-membranar diffusion of the copper atoms through the honeybee's organism as well as due to the fact that they show a phagoinhibitive action (anorectic action) in respect to the food intake by the honeybees.

The intensity of the phagoinhibitive action in regard to the concentrations, complies to an algebric law, the analysis of which can be performed in a detailed manner.

The obtained results as shown under FIG. 1 have been obtained from studies carried out in the laboratory, on batches of 100 honeybees each, located in small coops called small cases (logettes) in the absence of queen bees. The feeding made available to the honeybees, is placed in a graduated tube which allows the measurement of the ingested amount every day. The experiments have been carried out simultaneously with various small cases each receiving for the feeding of the honeybees a syrup of sucrose at 2 kg for 1 l water (i.e. 66% weight/weight) containing variable amounts of copper sulphate. (The length of the vertical lines corresponds to each point and shows the dispersion of the obtained results according to a classical expression of statistical determination).

Figure 1:
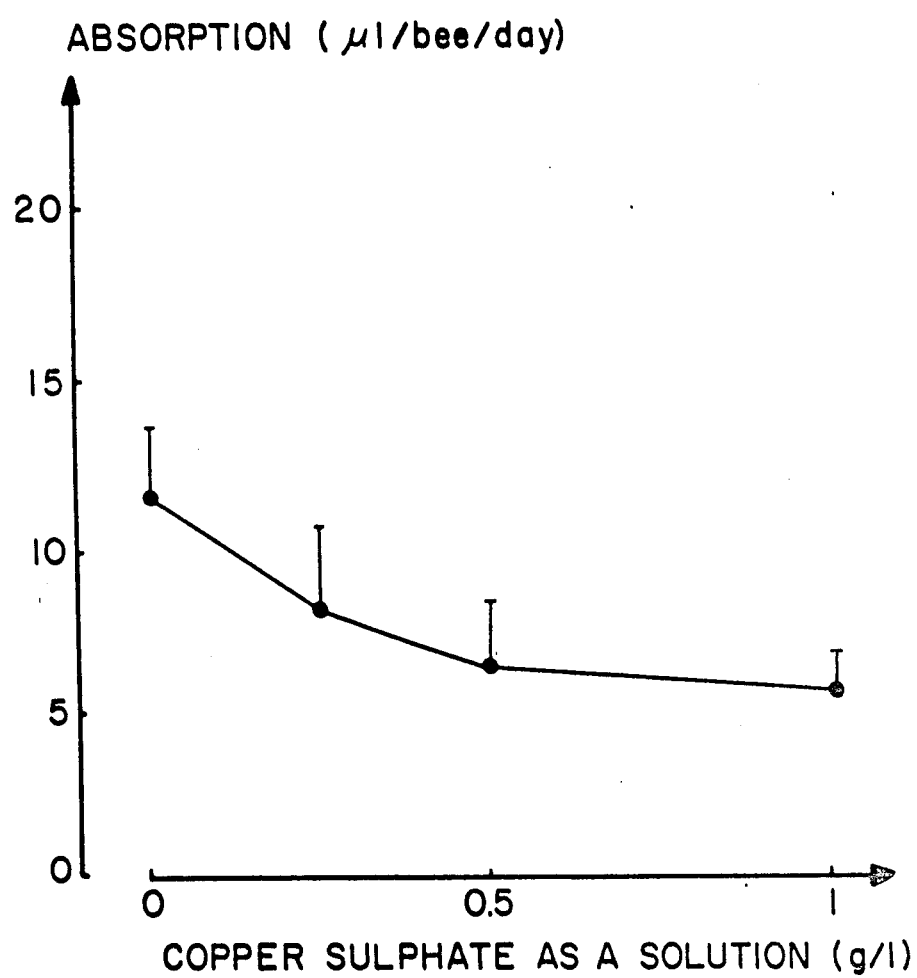
FIG. 1 is a plot of absorption of copper sulfate in ml/be/day plotted against copper sulfate as solution in grams/liter, showing the intensity of the phagoinhibitive action as a functional concentration of copper sulfate.

The copper salts used in this invention, have a copper content that generally ranges between 12 and 30%, and offers many advantages in regard of the mineral salts by the mere fact they have:

an appentency for the honeybees a good penetration inside the organism of the honeybees a strong antiparasitic activity towards Varroa jacobsoni a lack of cumulative storage of copper in the inner part of the organism of the honeybees.

Contrarily to almost all the pesticides, the copper salts according to this invention do not cause any contamination of the produced honey, neither by accumulation of copper nor by introduction of toxic molecules in the hives. They do not lead to any alteration of the organoleptic qualities of the honey.

Their solubilities in water and in the solutions of sucrose generally utilized for the feeding of the honeybees, as well as their excellent stability, moreover allow a marked easiness of use in the form of powder, solutions, candies (this word is intended to designate compositions based on sugar, of pasty consistance usually utilized by the bee-keepers) or even, of pastes, optionally admixed with other active ingredients.

The organic copper salts according to this invention, have the formula

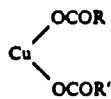

(I)

wherein the radicals R and R' —which may be the same or different are selected from the group consisting of:
- polyhydroxylated hydrocarbon chains, having from 2 to 12 carbon atoms, such as citric acid, tartaric acid or gluconic acid.
- linear or cyclic hydrocarbon chains which are substituted with an amino group, such as leucine, isoleucine or valine—having from 2 to 10 carbon atoms.
- hydrocarbon chains which are straight or cyclic, substituted with 2 to 4 amino groups and a carboxylci group, having from 2 to 10 carbon atoms, such as lysine or diaminopimelic acid.
- hydrocarbon chains substituted with an amino group and an amido group such as glutamine.
- hydrocarbon chains substituted with one or several hydroxylated group and with one or several carboxylated group, having from 2 to 10 carbon atoms such as Uronic acids or saccharic acids.

They are namely:

Copper gluconate or saccharate
$C_{12}H_{22}O_{14}Cu$  MW = 453,8  Cu % = 14
blue cristalline powder which is very soluble in water Copper glucoheptonate
$C_{14}H_{26}O_{16}Cu$  MW = 513,9  Cu % = 12,35
green cristalline powder very soluble in water
MP = 152°  $[\alpha]_D^{20}$ = −0,84°  (c = 1% w)

Copper glycinate
$C_4H_8N_2O_4Cu$  MW = 211,6  Cu % = 30
dark-blue crystalline powder  MP = 270°

Copper leucinate
$C_{12}H_{24}N_2O_4Cu$  MW = 323,9  Cu % = 19,6
blue-grey crystalline powder, water solubility at 20° C. = 1%
MP = 270° (dec)

Copper isoleucinate
$C_{12}H_{24}N_2O_4Cu$  MW = 323,9  Cu % = 19,6
dark-blue crystalline powder, water solubility at 20° C. = 1%
Mp = 245°

Copper l-aspartate
$C_8H_{12}N_2O_8Cu$  MW = 327,7  Cu = 19,4%
Navy blue crystalline powder, water solubility at 20° C. = 1%
MP = 250°

Copper l-glutamate
$C_{10}H_{16}N_2O_8Cu$  MW = 355,8  Cu % = 17,85%
blue crystalline powder, water solubility at 20° C. = 4%
MP = 262°

Copper Asparaginate
$C_8H_{14}N_4O_6Cu$  MW = 325,8  Cu = 19,5%
blue-lilac crystalline powder, water solubility at 20° C. = 0,5%
MP > 300°

Copper lactate
$C_6H_{10}O_6Cu$  MW = 241,7  Cu = 26,3%
light blue crystalline powder, water solubility at 20° C. = 8%
MP = 266°

Copper citrate
$C_6H_4O_7Cu_2$  MW = 315,2  Cu = 40,3%
blue crystalline powder, water solubility at 20° C. = 1%
MP = 246°

Copper citrate
$C_{12}H_{10}O_{14}Cu_3$  MW = 563,36  Cu = 33,3%
water solubility at 20° C. = 10%  MP = 246°

Copper gluconate/glucoheptonate
$C_{13}H_{24}O_{15}Cu$  MW = 483,9  Cu = 13,2%
Turquoise-blue crystalline powder, very soluble in water
MP = 155°  $[\alpha]_D$ = −0,3°  (c = 1% w)

Copper gluconate/aspartate
$C_{10}H_{17}NO_{11}Cu$  MW = 390,75  Cu = 16,25%

Copper gluconate/glutamate
$C_{11}H_{19}NO_{11}Cu$  MW = 404,8  Cu = 15,7%

Copper l-pyrrolidone carboxylate
$C_{10}H_{12}N_2O_6Cu$  MW = 319,8  Cu = 18,8%
hydrated with 7.15% water - blue crystalline powder
MP = 250° (dec)  Cu = 18,55%

All these compounds may be more or less solvated with molecules of water. Further these compounds may be in the form of stoechiometric, or non-stoechiometric addition salts or in the form of complex salts.

Furthermore instead of using the already synthetised copper salts, it may be also of value to use a mixture of an organic carboxylic acid of the formula

R COOH and/or

R' COOH wherein R and R' have the above-given definitions and a basic derivative of copper selected from the group consisting of copper Carbonate, copper basic carbonate, copper oxides or copper hydroxides in stoechiometric or non-stoechiometric ratio in order to produce "in situ" the copper salt of formula I.

In a more specific manner gluconic acid or an alkali-metal glyconic acid salt or an earth alkali-metal gluconic acid salt may be used in an aqueous medium in admixture with copper oxide or copper carbonate and thus producing by metathesis, the desired copper gluconate in solution.

This invention relates to the use of the salts of formula I as shown above, as well as such or in the form of compositions such as aqueous solutions, syrups, pastes and candies, in which they may be admixed wait inert carriers, or with nourishing materials for the honeybees, or with other active ingredients which, optionally show a complementary antiparasitic activity.

The specific advantages which may be drawn from the use of the copper derivatives according to this invention, for the treatment of Varroatosis of the honeybees, have been evidenced by a course of experiments which have demonstrated:

1°—A specific distinctive action against *Varroa jacobsoni* shown by the counting of the eliminated Varroas, when the hives are treated by nourishing materials with copper gluconate at different doses (0 g/l-0.2 g/l-0.5 g/l).

The honeybees have been fed with syrup of sucrose at 66% w/w containing increasing concentrations of Copper Gluconate. The whole amount of syrup made available to the honeybees was absorbed every day, that fact providing supplemental proof of the appentency of the honeybees toward the tested product.

Each hive was provided at its lower part with a plastic plate coated with a consistent grease. Each day at the same time, the plate was discarded and the counting of the Varroas fallen on the plate, was carried out. A grid surmounting this plate avoid that the honeybees may spontaneously proceed with the discharge of the Varroas.

Figure 2:
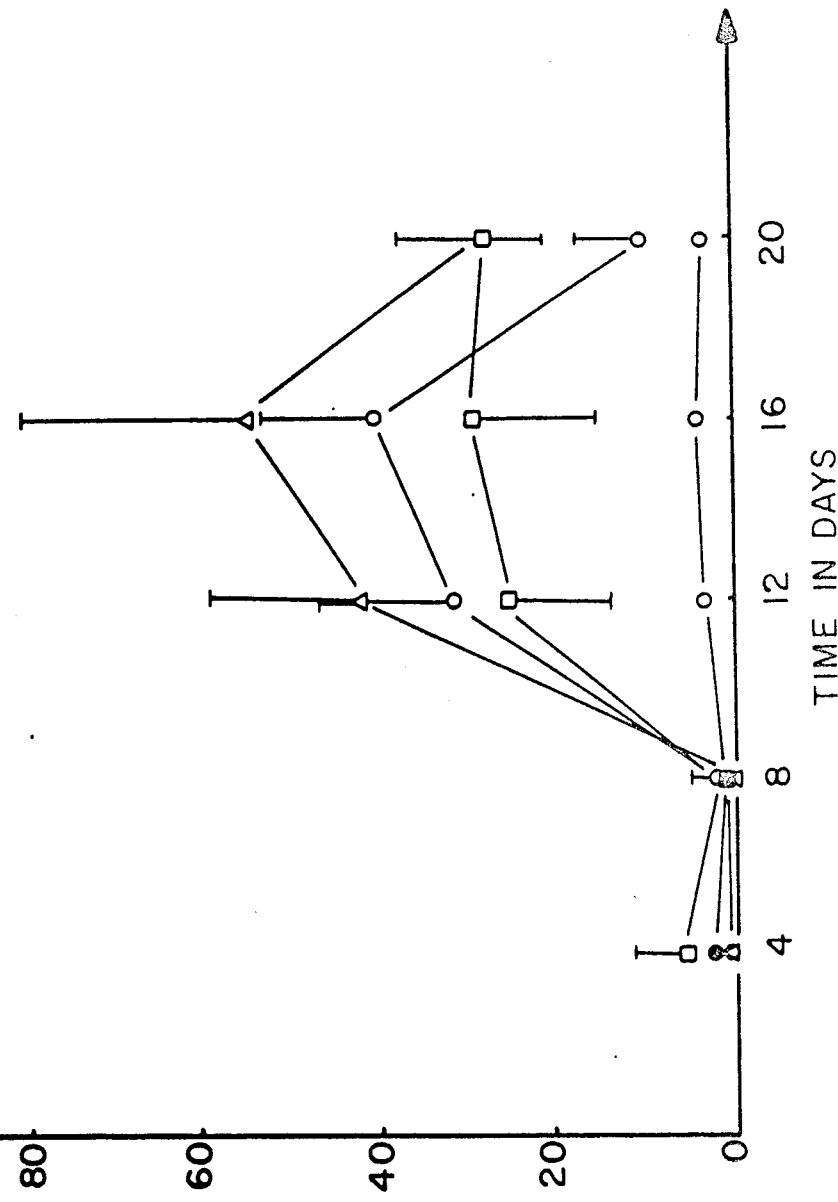
FIG. 2 is a multiple plot of all off of varroas against time in days for various dosages of copper gluconate.

The results shown in FIG. 2 have been obtained following experiments performed at full size in hives containing from 20,000 to 50,000 honeybees.

2°—The efficiency of the treatment has been defined as the ratio between the number of Varroas subsiding in the various colonies of an apiary after treatment by solutions at various concentrations, and the number of Varroas contained in the control hives, these two figures have been measured after treatment with Amitraze.

This experiment has been carried out in a series of 14 hives and the result thereof are compiled in the Table 3 figuring herein after.

TABLE 3

Fall of the Varroas after nourrishing with Copper Gluconate at various concentrations.

| HIVES N°... | TREATMENT | FALL OF THE VARROAS | EFFICIENCY |
|---|---|---|---|
| 1,6 | 0 g/l | 820 ± 380 (2) | |
| 2, 3, 4, 5, | 0,2 g/l | 165,5 ± 84,1 (4) | 79,8% |
| 7, 8, 9, 10 | 0,5 g/l | 207 ± 172 (4) | 74,7% |
| 11, 12, 13, 14 | 1 g/l | 109 ± 141 (4) | 86,7% |

These experiments allow to obtain the results of Table 3 above, and were carried out in full size on a set of 14 hives.

Each hive was given 6.75 l of syrup of sucrose at 66% w/w at various concentrations of copper gluconate ranging from 0.02 to 0.5 g/l. The syrup was totally ingested and no increase in the percentage of lethality in the honeybees was noted compared to that of the controls.

Measurements of the falls of the Varroas have been performed, at first, every day then every three days starting from the initiation of the delivery of the syrup.

To this end, a plate coated with a consistent grease was arranged at the bottom of each hive and protected with a grid as above-mentioned, in order to allow the counting of the Varroas. The fall begins to be significative in relation to the control hives which have only been given pure sugar syrup, after absorption by the honeybees of 3 liters of syrup per hive in 10 days.

As it may be stated from the examination of the figures of the Table, Copper Gluconate appears to be efficient even at low doses.

The counting of the remaining Varroas has been performed 2 days after the last delivery of syrup while submitting each hive to a treatment of shock by means of an acaricide (in these circumstances the marketed composition sold under the Tread Name AMITRAZE). It has been accepted that this treatment is efficient in the whole Varroas living on the honeybees, with the exception of the larvae which may exist in the operculated cells.

The efficiency of the treatment with Copper Gluconate is determined in ascribing the number of Varroas fallen during the treatment to the total number of Varroas resulting from the addition of fallen Varroas and existing Varoas.

The averages and the standard deviations have been calculated for the number of performed measures corresponding to the number of hives, this figure being mentioned between hyphens following the figures of the third column in Table 3.

The statistical calculation leads to a mean efficiency of 80±6% with respect to the control hives. A very significant advantage of the copper derivatives according to this invention results in the fact that they can be continuously given during long sets of time, which allows the destroying of the parasites in proportion as they emerge from operculated cells while it is not possible when acaricides are utilized —such as Amitraze more particularly, due to their toxicity for the honeybees.

The copper derivatives according to this invention allow the control of the infestation by the parasites and the prevention of the re-infestation.

These derivatives according to the invention, are incorporated by the worker bees during the nourishment of the larvae and cause their efficiency in the parasites, protected from the pesticides, by the opercules of the cells.

Not any of the presently known treatments may be protracted without damaging the life of the honeybees and the quality of the products provided by them.

This is particularly the case of the pesticides which besides their toxicity against the honeybees, are incorporated in the wax and give rise to splitting products of the molecule, in the honey.

In contrast thereof, when the products according to this invention are utilized, a lack of noxiousness for the honeybees have been noted for the two following reasons:

1. the organic moiety of the copper salts according to this invention is neither harmful nor susceptible to provide by degradation, toxic metabolites.

2. the copper given in the form of salts according to this invention, does not generate any accumulation either in the honey or in the body of the honeybees themselves.

The figured facts have been evidenced by means of studies performed in full size on a group of 64 hives, 49 of which have been fitted with supers.

The results are given in Table 4 hereafter, in which the first column relates to the whole amount of copper given during this period the second to the amount of copper found in mg/kg of honey in the body of various hives and the third to the amount of copper in mg/kg of honey extracted from the supers.

The amounts of copper have been determined through atomic absorption using a spectrograph (Perkin Elmer spectrograph 420). The measures are performed after having extracted the totality of the honey on a mean sample.

TABLE 4

Residual Amounts of Copper as determined in samples of honey taken out after 7 ± 1 months following administration of copper gluconate (n = number of measure)

| Total amount per Hive | Body of the hive in mg/kg of copper | SUPER in mg/kg of copper |
|---|---|---|
| 0,0 g (Controls) | 3,4 ± 1,9 (N = 9) | 4,2 ± 3,3 (N = 3) |
| 1,25 g | 5,3 ± 2,5 (N = 28) | 2,7 ± 1,7 (N = 19) |
| 2,50 g | 1,0 ± 0,25 (N = 21) | 0,8 ± 1,0 (N = 21) |
| 3,00 g | 1,6 ± 1,0 (N = 6) | 0,6 ± 0,1 (N = 6) |

It has so been found that the residual amount of Copper is not proportional to the amount of copper derivative given and that a very small but unnegligible amount of copper appears in the honey harvested in the hives, even those which have not received any copper derivative. The differences are not statistically-significant.

The utilization of the organic salts of copper, according to this invention offers a very marked advantage with respect to that of the mineral salts of copper and more precisely that of copper sulphate, since they are metabolized in the body of the honeybees and hence the accumulation of copper in the honey is much lower, as it appears from the two Tables appearing hereinafter, which corresponds to comparative experiments performed on one side with copper glyconate (A) and on the other side with copper sulphate (B).

TABLE A

| Total Amount per Hive | Doses of mineral copper | Content in copper in the honey in the bodies of the hives mg/kg |
|---|---|---|
| 0 g | 0 g | 0,674 ± 0,065 (N = 2) |
| 1,35 g | 0,189 g | 0,686 ± 0,084 (N = 4) |
| 3,38 g | 0,473 g | 0,836 ± 0,296 (N = 4) |
| 6,75 g | 0,945 g | 0,656 ± 0,014 (N = 4) |

TABLE B

| Total Amount per Hive | Doses of mineral copper | Content in copper in the honey in the bodies of the hives mg/kg |
|---|---|---|
| 0 g | 0 g | 1,98 ± 2,03 (N = 2) |
| 1,25 g | 0,319 g | 4,37 ± 2,89 (N = 4) |
| 2,00 g | 0,510 g | 8,03 ± 10,46 (N = 4) |

It has been stated that, while the amounts of copper given in the form of glyconate have been far higher, the content of copper in the honey is much lower than that found after administration of copper sulphate.

The fact that it does not incur any storage of copper inside the body of the honeybees is shown in FIGS. 3 through 6.

These four graphs make apparent the amounts of copper fixed inside the body of the hives as a function of time (in days) and the amount of ingested copper during the same period of time, as a function of the content of copper glyconate in the nourishing syrup.

Figure 3:
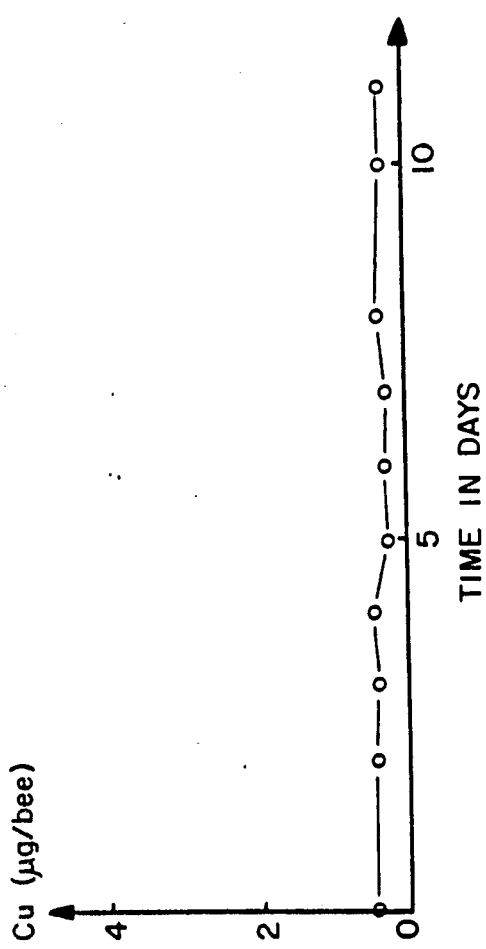
FIG. 3 shows the level of copper in bees over a given period of time in which the bees are fed syrup only.

The FIG. 3 corresponds to the control bees which receive only the syrup (i.e 0 g/l).

Figure 4:
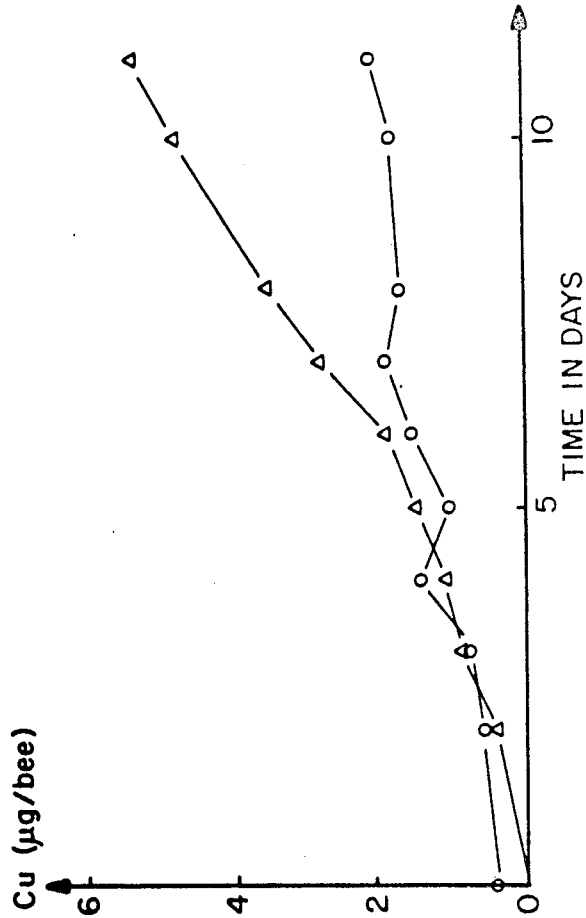
FIG. 4 is a comparative plot of copper absorbed by bees over a given period of time when fed copper gluconate of copper sulphate.
Figure 5:
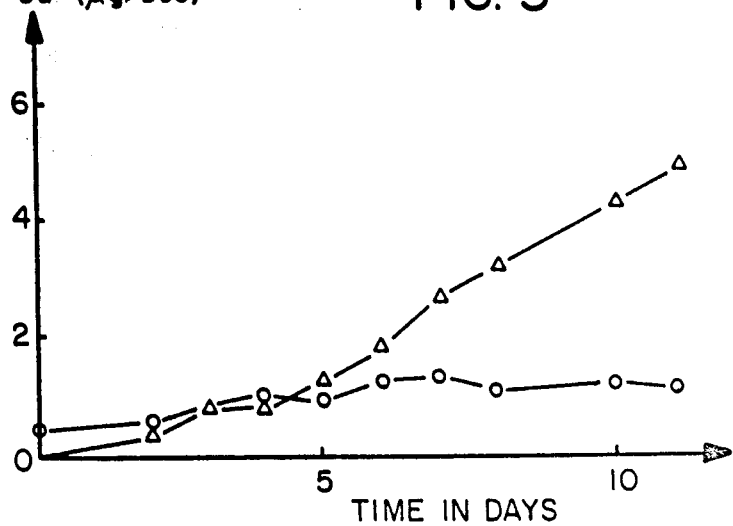
FIG. 5 is similar to FIG. 4 at a different dosage level.
Figure 6:
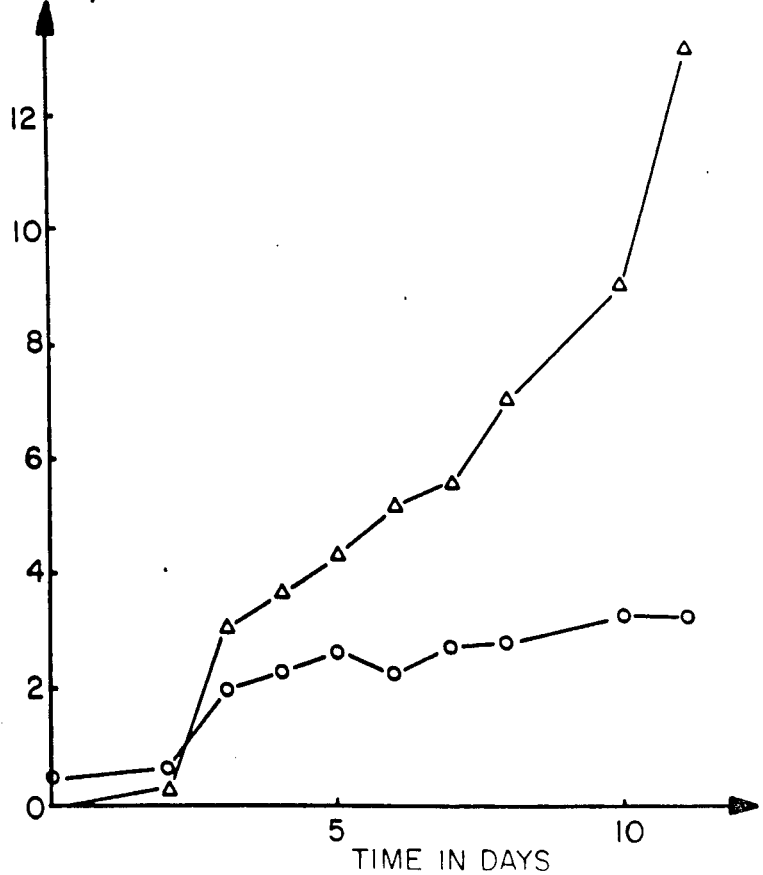
FIG. 6 is similar to FIG. 5 but at a different dosage level.

The FIG. 4 corresponds to a feeding at 0.2 g/l of copper. The FIG. 5 corresponds to a feeding at 0.3 g copper/l and FIG. 6 corresponds to a feeding at 0.5 g/l copper.

The determination of the amounts of copper inside the bodies of the honeybees is performed through atomic absorption on samples of 5 honeybees after crushing and centrifuging them, and analysis of the supernatant liquid.

EFFECT ON THE APPENTENCY OF THE HONEYBEES

The compounds according to this invention —and particular copper glyconate— further show a marked advantage due to the fact of the great appentency of the honeybees in respect of them.

The determinations of appentency have been carried out on batches of 100 honeybees located inside small cases to which the compounds have been offered in the usual nourishing solutions of sucrose at 66% w/w, from a graduated tank which allows the measurement of the consumed amount per day.

Figure 7A:
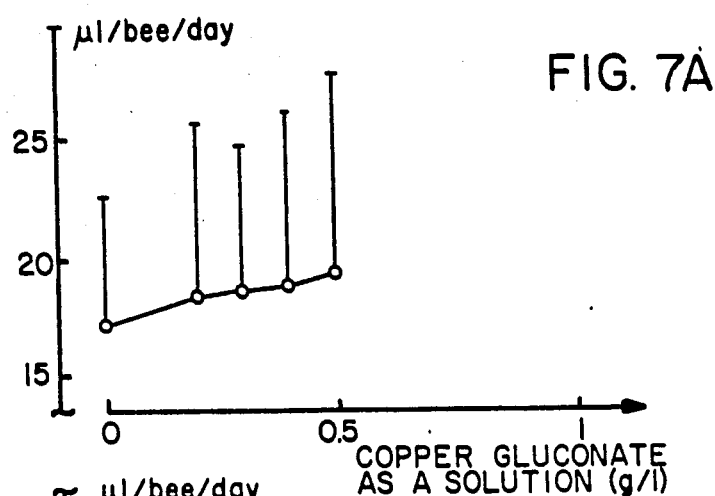
FIG. 7A is a plot of absorption in ml/bee/day against concentration of copper as copper gluconate in the presence of pollen.
Figure 7B:
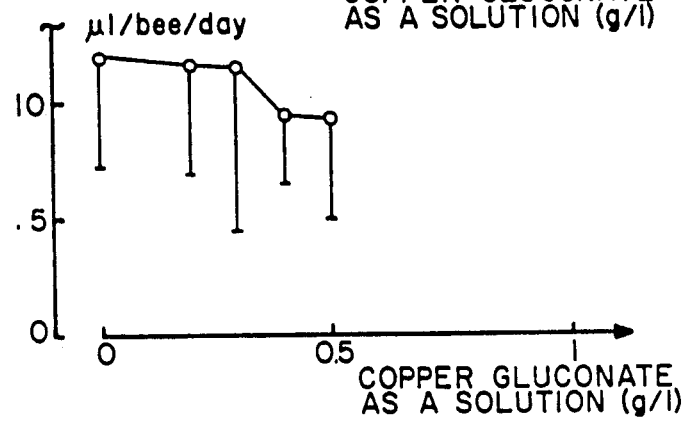
FIG. 7B is a plot similar to 7A without the presence of pollen.
Figure 7C:
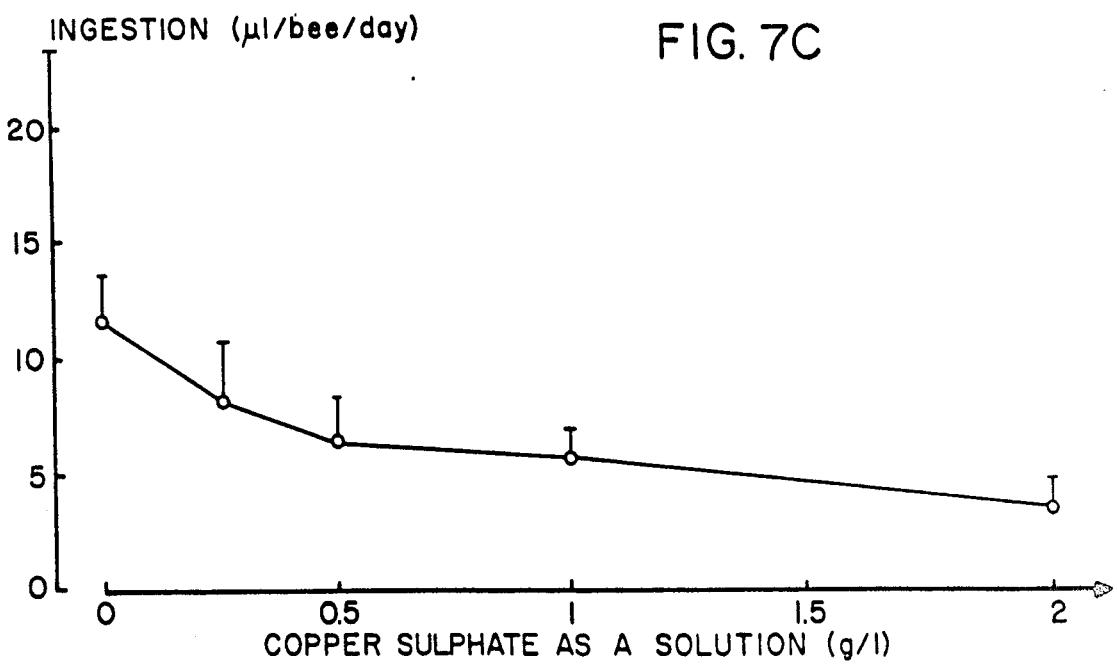
FIG. 7C is similar to the plot of FIG. 7B where copper sulphate replaces copper gluconate.
Figure 8A:
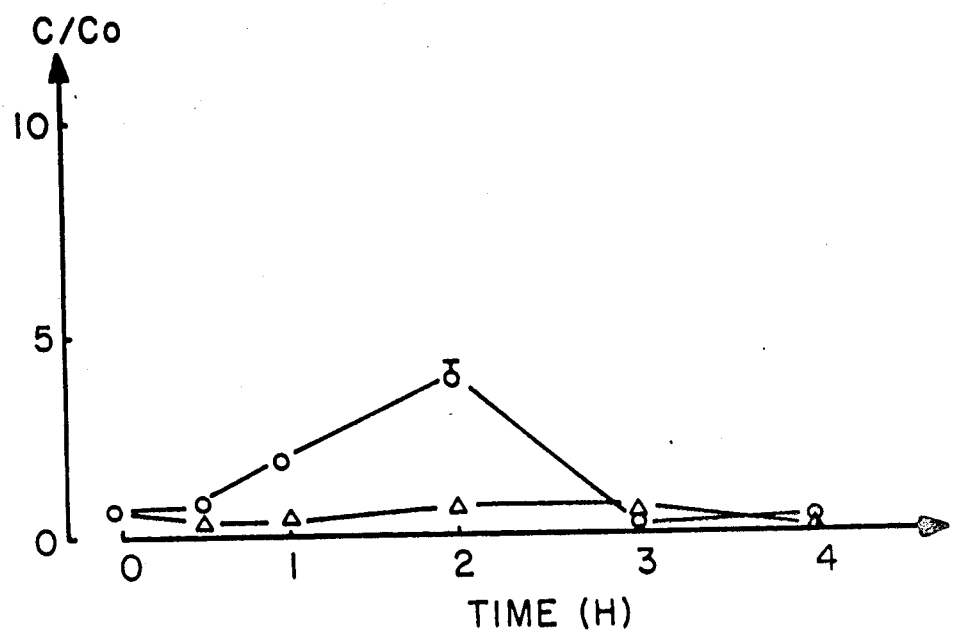
FIGS. 8A through 8D are plots of glucosemia and trehalsemia against time for various levels of copper gluconate administration.
Figure 8B:
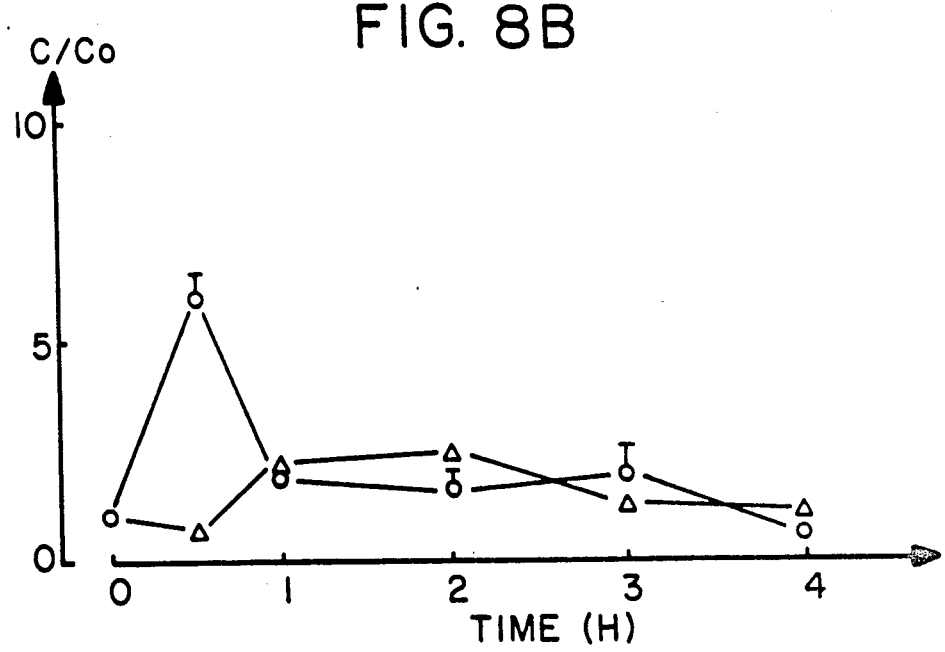
Figure 8C:
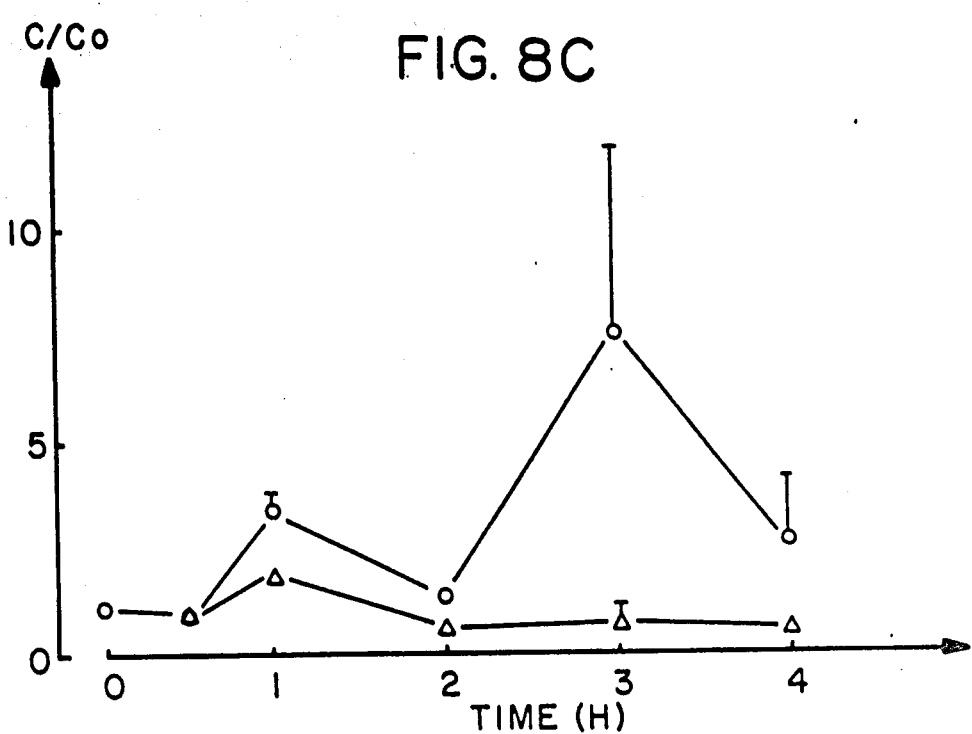
Figure 8D:
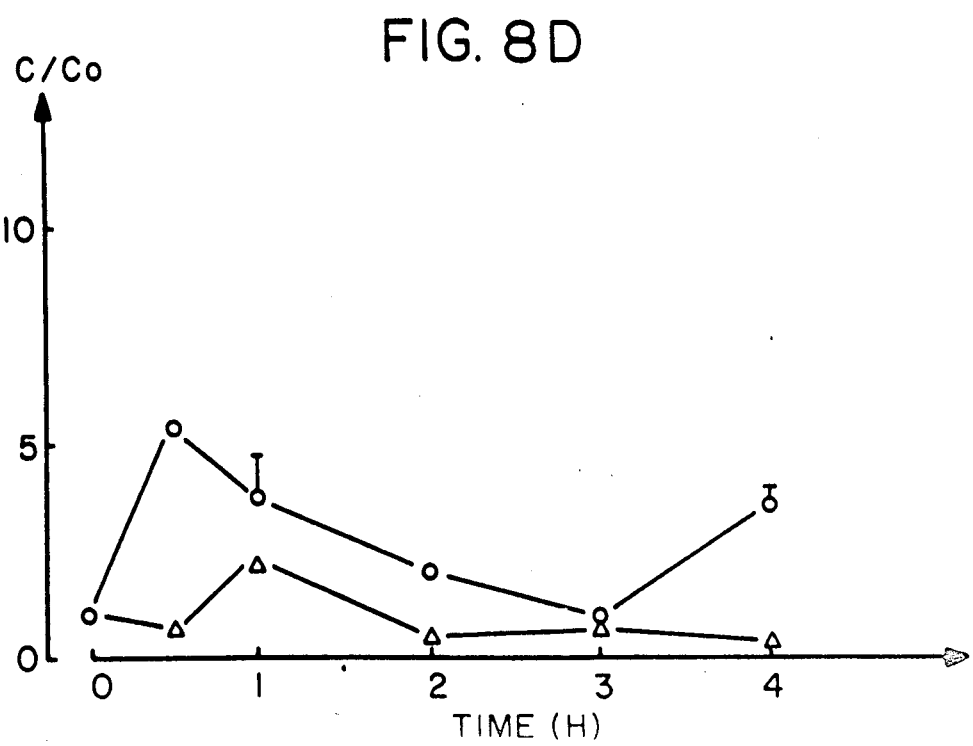

The results obtained with copper glyconate are given with the curves of the of FIGS. 7A through 7C, in which the FIG. 7A corresponds to nourishing with copper glyconate and supply of pollen, FIG. 7B to nourishing with copper glyconate without supply of pollen and FIG. 7C to nourishing with copper sulphate without supply of pollen.

It should be noted that the pollen has been made available to the honeybees in a sufficient amount inside the small cases, without being admixed to the syrup.

The determinations have been performed every day and the length of the vertical bars of the diagrams hereabove, are proportional to the deviation of the observed results. They evidence a clearly higher appentency in the case of the utilization of the compounds of this invention.

The results mentioned in the preceding paragraphs substantially relate to experiments performed by means of Copper Gluconate. Similar results related to the destroying of the Varroas have been obtained using the other compounds according to this invention and particularly those mentioned on pages 4, 5 and 6 hereabove, and comparative tests of appentency have been carried out using the same method as previously given. The results of these tests are gathered in Table 7 hereinafter in which the figures correspond to measures performed on honeybees placed in small cases, having pollen to their disposal, and are means expressed in microliters per honeybee and per day for N countings. These figures have to be compared to the appetency for pure sugar syrup which is of 21.13±6.31 microliters per honeybee and per day (value obtained for N=16 measures).

Apart from the role played by the presence of atoms of copper, the organic moiety of these molecules according to the invention plays a marked role on the appentency of the honeybees toward these copper derivatives.

ACTION ON BIOLOGICAL ACTIVITY

It has further been shown that this organic moiety play a significant role in the metabolism of the honeybees. This is particularly true in the case of copper gluconate, the ingestion of which by the honeybees causes —even a very low dose— a momentaneous and significative increase of the glycosemia in the honeybees which stimulates their activity and increases the production of honey.

TABLE 7
COMPARATIVE APPETENCIES FOR VARIOUS COPPER SALTS
Note: The averages and standard deviations are calculated for N-experiments.
Appetency for pure cane sugar syrup is 21,13 ± 6,31 microliters/bee/data for N =

| | PRODUCT ABSOLUTE VALUES | | | | | 1/1 COPPER GLUCO-NATE | RELATIVE VALUES/ PURE SUGAR SYRUP | | |
|---|---|---|---|---|---|---|---|---|---|
| CONCENTRATION M.M. | 0,44 | 0,61 | 1,1 | 1,54 | 2,4 | | TEST 1 | TEST 2 | AVERAGE |
| COPPER GLUCONATE | 22,3 ± 2,5 (N = 15) | — | 21,2 ± 2,6 | — | — | — | 105,5% | 100,3% | 102,9% |
| COPPER GLUCO-HEPTONATE | 15,68 ± 2,35 (N = 16) | — | 14,58 ± 3,16 (N = 16) | — | — | 14,90 ± 3,64 | 74,2% | 69,0% | 71,6% |
| COPPER GLYCINATE | 16,65 ± 5,01 (N = 16) | — | 15,5 ± 5,03 (N = 16) | — | — | 14,30 ± 3,52 (N = 11) | 78,0% | 73,7% | 75,85% |
| COPPER SOLEUCINATE | — | 16,69 ± 5,03 (N = 51) | — | 13,57 ± 5,77 (N = 53) | 13,79 ± 5,73 (N = 46) | — | 78,9% | 64,2% | 71,55% |
| COPPER ASPARTATE | — | 17,96 ± 7,20 (N = 89) | — | 14,68 ± 5,40 (N = 77) | 12,49 ± 5,11 (N = 73) | — | 76,5% | 69,4% | 55,1% |
| COPPER GLUTAMATE | 16,18 ± 4,66 (N = 16) | — | 16,64 ± 7,97 (N = 16) | — | — | 11,56 ± 6,32 (N = 10) | 76,5% | 78,7% | 77,6% |
| COPPER ASPARAGINATE | 15,48 ± 4,32 (N = 11) | — | 11,97 ± 3,34 (N = 12) | — | — | 12,21 ± 4,29 (N = 10) | 73,2% | 56,3% | 65,0% |
| COPPER LACTATE | 15,30 ± 4,24 (N = 12) | — | 15,60 ± 4,34 (N = 12) | — | — | 10,95 ± 3,54 (N = 9) | 72,4% | 73,8% | 73,6% |
| COPPER CITRATE | 14,71 ± 4,25 (N = 15) | — | 12,67 ± 3,96 (N = 15) | — | — | 12,67 ± 3,96 (N = 15) | 69,5% | 60,0% | 64,75% |
| COPPER LEUCINATE | 15,83 ± 4,53 (N = 15) | — | 13,02 ± 2,42 (N = 15) | — | — | 13,02 ± 2,42 (N = 15) | 74,0% | 61,6% | 67,8% |

This action results —as shown in the diagrams of FIGS. 8A through 8D hereinafter— from an increase of the activity of the Trehalases (enzymes which release glycose in the organism of the honeybees from a precursor stored in the hemolymph). These diagrams evidence the action of copper glycinate on the glycosemia of the honeybees after ingestion of increasing doses of this product.

Figure 9A:
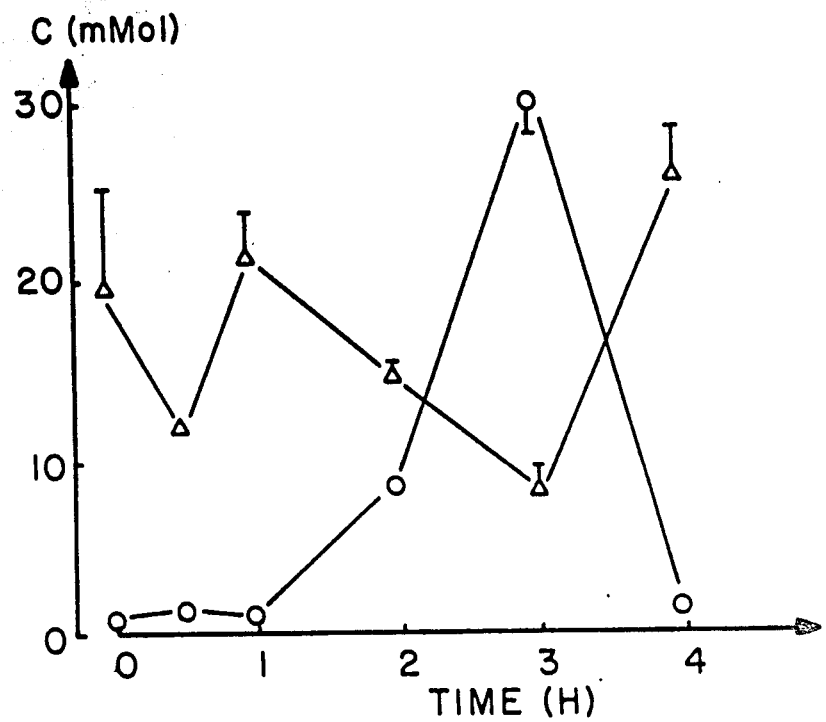
FIGS. 9A and 9B show the concentration of glucose and trihalases in the hemolymph of honey bees against time following ingestion of copper gluconate.
Figure 9B:
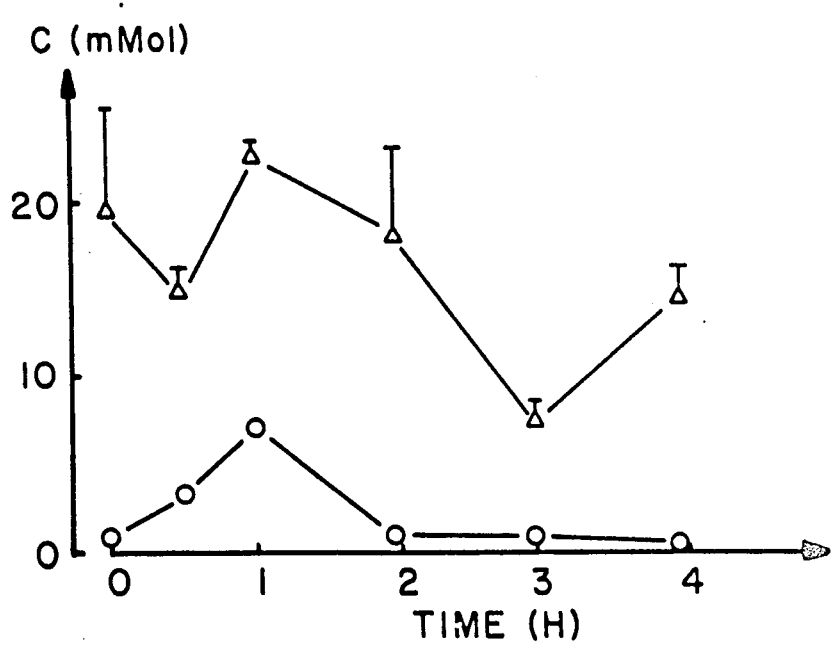

The increase in the concentration of glucose and trehalases in the hemolymph of the honeybees following the ingestion of copper glycinate is shown by FIGS. 9A and FIG. 9B hereinafter:

FIG. 9A corresponds to experiments performed without administration of an inhibitor of trehalases FIG. 9B is with administration of such an inhibitor.

Figure 10A:
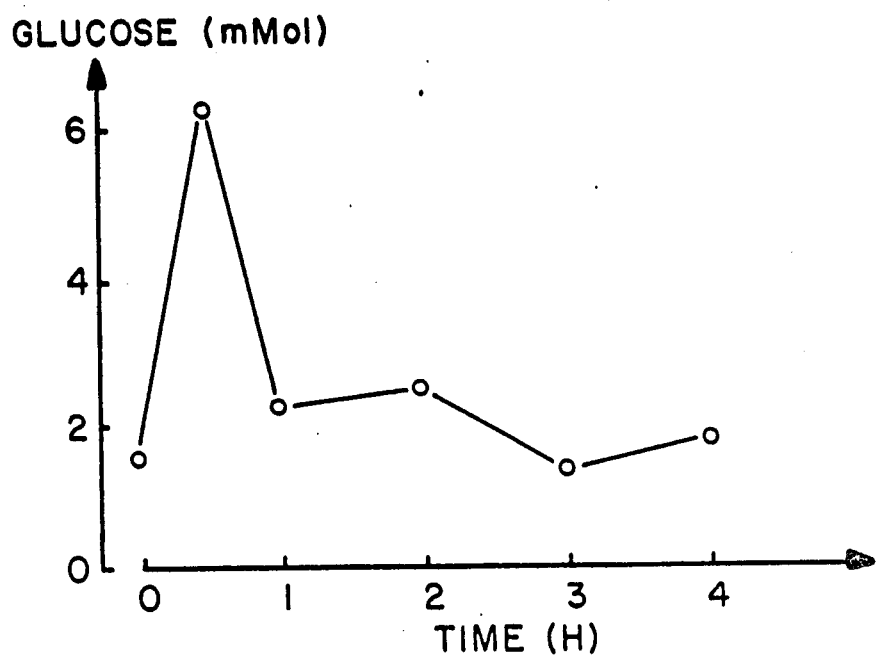
FIG. 10A shows glycosemia activity against time following ingestion of copper gluconate.
Figure 10B:
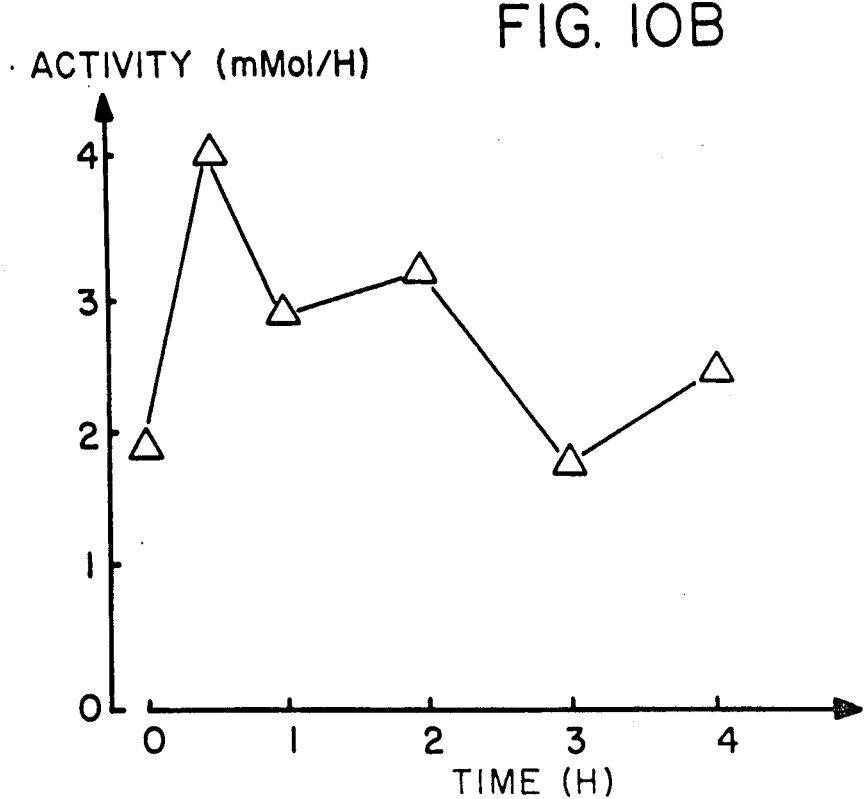
FIG. 10B shows trihalase activity in the hemolymph against time after similar ingestion.

FIG. 10A further evidences the variation of the glucosemia in the honeybees following the ingestion of copper glycinate. FIG. 10B shows the variation of activity of the trehalases in the hemolymph of the thus treated honeybees.

It has already been disclosed that glucose contained in the hemolymph is the main source of energy for the honeybees and an increase of the content of this substance in the hemolymph —correlated to the ingestion of copper glycinate— is a factor which improves the productivity of the hives. Independently from the increase in the production of honey, this action is to be estimated by the increase in the activity of cleaning the hives shown by the honeybees.

Supplemental advantages may then be obtained apart from the destroying of the Varroas, by the use of copper glycinate. A similar effect has been shown by other copper derivatives according to this invention, particularly by copper glycoheptonate, by copper glycinate/glucoheptonate, copper gluconate/glutamate.

The use of copper salts which contain a nitrogen atom, also exerts a favourable effect on the metabolism of the honeybees. The pollen they collect is one of the main sources of nitrogen containing ingredients which they need.

The supplemental contribution obtained by the use of compounds according to this invention is a non-negligible factor which promotes the productivity of the hives.

CONCLUSION

The utilization of the copper derivatives according to this invention allows to fight in a systemic manner, *Varroa jacobsoni* without altering the quality of the honey, and the wax, and without impairing the good health of the honeybees which is a factor of equilibrium for their activity and for the production of the hives.

What is claimed is:

1. A method of treating honeybees contaminated with acarian parasites which comprises feeding to said bees, an ingestible aqueous solution of at least one organic copper salt at a concentration up to 1 g. copper/l., having the formula:

in which R and R', may be the same or different, and are selected from the group consisting of:
polyhydroxylated hydrocarbon chains having from 2 to 12 carbon atoms, straight or cyclic hydrocarbon chains bearing an amino radical, having from 2 to 4 carbon atoms,
linear or cyclic hydrocarbon chains having from 2 to 10 carbon atoms, substituted by from 2 to 4 amino groups in the presence of a carboxylic group,
hydrocarbon chains having both an amino group and an amido group, hydrocarbon chains having from 2 to 10 carbon atoms bearing one or several hydroxyl groups in the presence of one or more carboxylic groups.

2. A method of claim 1, wherein the honeybees are contaminated by Varroa jacobsini.

3. A method of claim 1, wherein the copper salt is selected from the group consisting of glyconate, saccharate, glycoheptonate, glycinate, isoleucinate, aspartate, asparate, asparaginate, lactate, citrate and mixtures of glyconate/glucoheptonate, glyconate/aspartate, glyconate/glutamate and pyrrolidone carboxylate with copper.

4. A method of claim 1, which comprises administering a solution of a equimolar amount of an organic carboxylic acid of the formula selected from the group consisting of RCOOH, R'COOH mixtures and salts thereof selected from the group consisting of alkali metal salts, earth alkaline metal salts with a basic copper derivative selected from the group consisting of carbonates, oxides and hydroxides.

5. A method according to claim 1 wherein at least one copper compound is admixed with an inert carrier or vehicle appealing to the appetite of the honeybees, at a concentration ranging from 0.2 to 1 g. copper/liter.

6. A method according to claim 5 wherein the inert diluents are powders, solutions, syrups and pastes.

7. A method according to claim 5 which comprises providing the copper compound to the population of a hive.

8. A process for stimulating the activity of the honeybees which comprises administering to a hive an alimentary composition having a concentration ranging from 0.25 to 16 NMol. of copper glyconate salts.

* * * * *